(12) United States Patent
Kitamoto et al.

(10) Patent No.: US 7,763,444 B2
(45) Date of Patent: Jul. 27, 2010

(54) KOJI MOLD-ORIGIN PHOSPHOLIPASE $A_2$

(75) Inventors: Katsuhiko Kitamoto, Tokyo (JP); Manabu Arioka, Tokyo (JP); Shotaro Yamaguchi, Kakamigahara (JP); Masayuki Machida, Tsukuba (JP); Keietsu Abe, Shiogama (JP); Katsuya Gomi, Sendai (JP); Kiyoshi Asai, Tokyo (JP); Motoaki Sano, Tsukuba (JP); Taishin Kin, Tokyo (JP); Hideki Nagasaki, Tokyo (JP); Akira Hosoyama, Tokyo (JP); Osamu Akita, Higashihiroshima (JP); Naotake Ogasawara, Ikoma (JP); Satoru Kuhara, Fukuoka (JP)

(73) Assignees: National Institute of Technology and Evaluation, Tokyo (JP); National Institute of Advanced Industrial Science and Technology, Tokyo (JP); National Research Institute of Brewing, Higashihiroshima-shi (JP)

( * ) Notice: Subject to any disclaimer, the term of this patent is extended or adjusted under 35 U.S.C. 154(b) by 0 days.

(21) Appl. No.: 12/489,827

(22) Filed: Jun. 23, 2009

(65) Prior Publication Data
US 2009/0263888 A1 Oct. 22, 2009

Related U.S. Application Data

(62) Division of application No. 10/547,708, filed as application No. PCT/JP2004/002566 on Mar. 2, 2004, now abandoned.

(30) Foreign Application Priority Data

Mar. 4, 2003 (JP) .............................. 2003-057565

(51) Int. Cl.
*C12N 1/15* (2006.01)
*C12N 15/74* (2006.01)
*C07H 21/00* (2006.01)

(52) U.S. Cl. .............. 435/69.1; 435/254.11; 435/320.1; 536/23.2

(58) Field of Classification Search ........................ None
See application file for complete search history.

(56) References Cited

U.S. PATENT DOCUMENTS 6,902,887 B1 6/2005 Berka et al.
7,148,032 B2 12/2006 Stringer et al.

FOREIGN PATENT DOCUMENTS

| JP | 06-327468 | 11/1994 |
|---|---|---|
| JP | 09-208492 | 8/1997 |
| JP | 10-155493 | 6/1998 |
| JP | 2002-101882 | 4/2002 |
| WO | WO-02/079476 | 10/2002 |

OTHER PUBLICATIONS

*Aspergillus oryzae* sequence AB126039.1.*
*Aspergillus flavus* sequence XM002383838.1.*
S. Wakatsuki et al., "Molecular cloning, functional expression and characterization of p15, a novel fungal protein with potent neurite-inducing activity in PC12 cells", Biochimica et Biophysica Acta 1522, 2001, pp. 74-81.
E. Soragni et al., "A nutrient-regulated, dual localization phospholipase $A_2$ in the symbiotic fungus *Tuber borchii*", The EMBO Journal Vo.20 No. 18, 2001, pp. 5079-5090.
The Supplementary Partial European Search Report for corresponding European Patent Application No. 04716373 dated May 11, 2006.
E. Soragni et al.; "A nutrient-regulated, dual localization phospholipase $A_2$ in the symbiotic fungus *Tuber borchii;*" The EMBO Journal; vol. 20, No. 18; pp. 5079-5090, 2001.
T.M. M Gress et al., "Hybridization fingerprinting of high-density cDNA-library arrays with cDNA pools derived from whole tissues," Mammalian Genome 3, 1992, pp. 609-619.
Wolcott, M.J., "Advances in Nucleic Acid-Based Detection Methods," Clinical Microbiology Reviews, Oct. 1992, pp. 370-386.
Alignment of polynucleotide sequence encoding SEQ ID NO:1 and W002/079476 SEQ ID NO:833.
SEQLIST of W002/079476 (available on WIPO website).
Alignment of polynucleotide sequence encoding SEQ ID NO:1 and US-6902887 SEQ ID NO. 54597.
UNIPROT: Q8X0U_NEUCR (integrated into UNIPROT/TREMBL with Sequence version 1 on 01.03.2002 (1 page).
Office Action dated Jul. 24, 2009, issued on the corresponding European patent application No. 04 716 373.8.

* cited by examiner

*Primary Examiner*—Scott Long
(74) *Attorney, Agent, or Firm*—Edwards Angell Palmer & Dodge LLP

(57) ABSTRACT

It is intended to provide koji mold-origin phospholipase $A_2$ and a DNA encoding it. Namely, phospholipase $A_2$ comprising the following protein (a) or (b): (a) a protein having an amino acid sequence represented by SEQ ID NO: 1 or 2; and (b) a protein having an amino acid sequence derived from an amino acid sequence represented by SEQ ID NO: 1 or 2 by a partial modification and serving as phospholipase $A_2$.

3 Claims, 5 Drawing Sheets

SEQUENCE LISTING

<160> NUMBER OF SEQ ID NOS: 12

<210> SEQ ID NO 1
<211> LENGTH: 222
<212> TYPE: PRT
<213> ORGANISM: Aspergillus oryzae

<400> SEQUENCE: 1

```
Met Lys Asn Ile Phe Val Ala Thr Leu Gly Leu Phe Ala Ala Val Ser
1               5                   10                  15

Ser Ala Leu Pro Tyr Thr Thr Pro Val Asn Asp Asn Pro Ile Ser Ala
            20                  25                  30

Leu Gln Ala Arg Ala Thr Thr Cys Ser Ala Lys Ala Thr Asp Asn Leu
        35                  40                  45

Ile Phe Lys Val Ser Met Lys Thr Phe Gln Lys Ala Arg Lys Ala Lys
    50                  55                  60

Asn Pro Ser Lys Cys Asn Trp Ser Ser Asp Asn Cys Ser Lys Ser Pro
65                  70                  75                  80

Asp Lys Pro Asp Gly Tyr Asn Phe Ile Pro Ser Cys Gln Arg His Asp
                85                  90                  95

Phe Gly Tyr Arg Asn Thr Lys Lys Gln Lys Arg Phe Thr Lys Ala Met
            100                 105                 110

Lys Lys Arg Ile Asp Asp Asn Phe Lys Lys Asp Leu Tyr Lys Tyr Cys
        115                 120                 125

Ser Gln Phe Ser Gly Trp Ser Ser Trp Lys Gly Val Glu Cys Arg Arg
    130                 135                 140
```

Leu Ala Asp Val Tyr Tyr Thr Ala Val Arg His Phe Gly Lys Arg Asp
145                 150                 155                 160

Glu Ala Leu Glu Phe Asp Pro Glu Val Glu Phe Lys Arg Asp Glu
            165                 170                 175

Val Ala Asp Val Gln Pro Asp Glu Phe Asp Asn Phe Gly Ser Glu
            180                 185                 190

Val Asp Pro Asp Ile Glu Gly Gln Val Ile Pro Glu Val Leu Glu Asp
        195                 200                 205

Asp Gly Val Asp Val Glu Asn Leu Asp Asp Ile Glu Asn Leu
        210                 215                 220

<210> SEQ ID NO 2
<211> LENGTH: 160
<212> TYPE: PRT
<213> ORGANISM: Aspergillus oryzae

<400> SEQUENCE: 2

Met Lys Ala Asn Ser Phe Leu Ile Ala Leu Leu Pro Thr Ala Leu Ala
1               5                   10                  15

Ile Pro Leu Pro Thr Pro Asn Glu Gly Ala Thr Ser Leu Ser Glu Ser
            20                  25                  30

Gln Arg Leu Gln Ser Ile Thr Asp Glu Leu Met Phe Gly Leu Glu Leu
        35                  40                  45

Pro Asp Phe Thr Ala Arg Arg Glu Ala Asn Asp Pro Pro Gln Leu Asp
    50                  55                  60

Trp Tyr Ser Asp Gly Cys Thr Arg Ala Pro Ser Asn Pro Leu Gly Phe
65                  70                  75                  80

Pro Phe Gln Arg Ala Cys Glu Arg His Asp Phe Gly Tyr Gln Asn Tyr
                85                  90                  95

Arg Ile Gln Gly Arg Phe Thr Lys Ala Ala Lys Ala Gln Ile Asp Leu
            100                 105                 110

Arg Phe Lys Glu Asp Leu Tyr Tyr Gln Cys Glu Leu Gly Arg Ala Val
        115                 120                 125

Gly Ile Cys Lys Lys Leu Ala Arg Leu Tyr Tyr Arg Ala Ser Gly Arg
    130                 135                 140

His Gly Gly Lys Asp Ala Ala Lys Arg Arg Glu Leu Asp Glu Leu Leu
145                 150                 155                 160

<210> SEQ ID NO 3
<211> LENGTH: 669
<212> TYPE: DNA
<213> ORGANISM: Aspergillus oryzae

<400> SEQUENCE: 3
atgaagaaca tcttcgttgc cactttgggc ctgttcgccg cagtttcgtc tgccttgccc      60
tacacaaccc ctgtcaatga caatcccatc tctgctttac aagcacgcgc gacaacatgc     120
tcggccaagg ccacggataa cctcatcttc aaggtctcca tgaagacctt ccagaaggcg     180
cgcaaggcca agaacccctc caagtgcaac tggtcatcgg acaactgctc caagtcaccc     240
gataagcccg atggatacaa cttcatcccc agctgccaaa gacacgattt cggctaccgg     300
aacacgaaga agcagaagcg cttcacaaag gccatgaaga gcgcattga cgacaacttc     360 aagaaggatc tctacaagta ctgcagccaa ttctcgggct ggagctcatg gaagggagtg     420
gagtgccgtc gccttgcgga tgtctactat actgctgtcc gccactttgg caagcgtgat     480
gaagcgcttg agtttgaccc tgaggttgag ttcgagaagc gtgatgaggt ggccgatgtc     540

```
cagcctgacg aatttgataa ctttgacggt tctgaagttg accctgatat cgagggccag    600
gtcattcccg aagttcttga agatgatgga gtggatgtgg agaacctcga cgatattgaa    660
aacctgtag                                                             669

<210> SEQ ID NO 4
<211> LENGTH: 593
<212> TYPE: DNA
<213> ORGANISM: Aspergillus oryzae

<400> SEQUENCE: 4
atgaaggcta acagctttct cattgccctc ctcccaaccg ccctagccat ccccctcccc     60
acaccaaatg aaggcgctac aagcctctca gaaagccagc gcctccagtc tatcaccgac    120
gagcttatgt tcggcctcga gctgcccgac ttcacagctc gcagagaggc aaacgaccct    180
cctcagttag actggtactc tgatggctgc acaagggctc cgagtaaccc tctcggattc    240
ccctttcaaa gggcgtgtga acgccatgac ttcggttacc agaactaccg aatacaaggg    300
cgcttcacca aggccgcaaa agcgcagata gatcttagat tcaaagaaga gtatgatttc    360
cctttcgttc cttccttctc ccctggaatc tgcttctgtt gattcttatg cagttggat    420 attgagagtc tggaggactg acgtttgatt cactgtttag tctttactat caatgtgaat    480
taggacgcgc tgtcggaatt tgcaagaagt tggctcggtt gtactaccgt gcttcggggc    540
ggcatggtgg taaagatgca gcgaagagaa gggagttgga tgaacttctt tag           593

<210> SEQ ID NO 5
<211> LENGTH: 1969
<212> TYPE: DNA
<213> ORGANISM: Aspergillus oryzae
<220> FEATURE:
<221> NAME/KEY: exon
<222> LOCATION: (1001)..(1666)

<400> SEQUENCE: 5
tgacctcata tagaagtgac gccgggccaa tgccaaaatt gaagctttta cgaagactaa     60
cctcggattt tttcttggca gagcttgacc tcgtattgcg tcaattgcga caattatcgc    120
tttcctggaa aatatcgcat attgaagaag tggcatgtat tgctgttagt gagtttggat    180
acgtatcaaa atactcctaa taaccagcaa ccaaaagaaa atgtgagcac tggtggaacc    240
gaattgtgtt atggcaggat agaattgaga atgggtttct tcagcggggg atcctccgat    300
gataaccttc tgagagctat ttttagaatc aagggtcttc cagcttgacg atcatcttgg    360
catacacaag cactacagct gcacgacgat ggggctttac gagtcacgaa ggtaacccaa    420
gattcttcac tgagtcttgg catgcgagcc atgctcgtac ctggatccct tttgtctgga    480
atttactatt attggatacg ataatgcctt gatccagggt cctttagaa ccaataggcc     540 actaaagctt acccgaggcc aatttatcct tcgaagtgaa tatgctcggt gcatttcagg    600
ttctgcagat cctgaagccc tttaccgtat cctgaatggt cttctcttct tctccaataa    660
tacgtcgagg gctttaatta tgttcgtgtt gagaactcgt aaagaaagac aaataggttc    720
ttggcgagag gggatagaat gcatcacgtc cacaatgcgg cacagggaat gtgccagacg    780
atacagcaga atggggcgg agcgagacgt agtttaccga gtacgaaata gcctcgttca    840
aggagacagt ccatggcaac cataagagtc attcgcgagt ataaagggca ggtcaactcc    900
tgtcatgtag ctctctacag aatcatcaac aatctcctct cgcaagcatc acatctactt    960
cttattgcct attctgtccg agtgctagcc acttatcatc atg aag aac atc ttc     1015
                                               Met Lys Asn Ile Phe
```

-continued

|   |   |   |   |   | 1 |   |   |   | 5 |   |   |   |   |   |   |
|---|---|---|---|---|---|---|---|---|---|---|---|---|---|---|---|

```
gtt gcc act ttg ggc ctg ttc gcc gca gtt tcg tct gcc ttg ccc tac      1063
Val Ala Thr Leu Gly Leu Phe Ala Ala Val Ser Ser Ala Leu Pro Tyr
             10                  15                  20 aca acc cct gtc aat gac aat ccc atc tct gct tta caa gca cgc gcg      1111
Thr Thr Pro Val Asn Asp Asn Pro Ile Ser Ala Leu Gln Ala Arg Ala
         25                  30                  35 aca aca tgc tcg gcc aag gcc acg gat aac ctc atc ttc aag gtc tcc      1159
Thr Thr Cys Ser Ala Lys Ala Thr Asp Asn Leu Ile Phe Lys Val Ser
     40                  45                  50 atg aag acc ttc cag aag gcg cgc aag gcc aag aac ccc tcc aag tgc      1207
Met Lys Thr Phe Gln Lys Ala Arg Lys Ala Lys Asn Pro Ser Lys Cys
 55                  60                  65 aac tgg tca tcg gac aac tgc tcc aag tca ccc gat aag ccc gat gga      1255
Asn Trp Ser Ser Asp Asn Cys Ser Lys Ser Pro Asp Lys Pro Asp Gly
 70                  75                  80                  85 tac aac ttc atc ccc agc tgc caa aga cac gat ttc ggc tac cgg aac      1303
Tyr Asn Phe Ile Pro Ser Cys Gln Arg His Asp Phe Gly Tyr Arg Asn
                 90                  95                 100 acg aag aag cag aag cgc ttc aca aag gcc atg aag aag cgc att gac      1351
Thr Lys Lys Gln Lys Arg Phe Thr Lys Ala Met Lys Lys Arg Ile Asp
            105                 110                 115 gac aac ttc aag aag gat ctc tac aag tac tgc agc caa ttc tcg ggc      1399
Asp Asn Phe Lys Lys Asp Leu Tyr Lys Tyr Cys Ser Gln Phe Ser Gly
        120                 125                 130 tgg agc tca tgg aag gga gtg gag tgc cgt cgc ctt gcg gat gtc tac      1447
Trp Ser Ser Trp Lys Gly Val Glu Cys Arg Arg Leu Ala Asp Val Tyr
    135                 140                 145 tat act gct gtc cgc cac ttt ggc aag cgt gat gaa gcg ctt gag ttt      1495
Tyr Thr Ala Val Arg His Phe Gly Lys Arg Asp Glu Ala Leu Glu Phe
150                 155                 160                 165 gac cct gag gtt gag ttc gag aag cgt gat gag gtg gcc gat gtc cag      1543
Asp Pro Glu Val Glu Phe Glu Lys Arg Asp Glu Val Ala Asp Val Gln
                170                 175                 180 cct gac gaa ttt gat aac ttt gac ggt tct gaa gtt gac cct gat atc      1591
Pro Asp Glu Phe Asp Asn Phe Asp Gly Ser Glu Val Asp Pro Asp Ile
            185                 190                 195 gag ggc cag gtc att ccc gaa gtt ctt gaa gat gat gga gtg gat gtg      1639
Glu Gly Gln Val Ile Pro Glu Val Leu Glu Asp Asp Gly Val Asp Val
        200                 205                 210 gag aac ctc gac gat att gaa aac ctg taggttttcg gcattggctc            1686
Glu Asn Leu Asp Asp Ile Glu Asn Leu
    215                 220 tacactttgc aaatgggtcg tcataatcca ttggaagccg gaggaggagg gaaatcaagg    1746
catcttttgg ttgtcagtaa ctttgagtgc ctagtttgtg aattgttttt tgaggttcta    1806
tttgaattct gcttttgttc aatcttatag cttcctacgt tgttgtcatt taaaaatgga    1866
caggagtatc tgtgagattt ttgacttgaa atcagtagca gtcaaccaat aaaagaatag    1926
caaatgcttc taccaatctt tggatctagt acataagtag aca                     1969
```

```
<210> SEQ ID NO 6
<211> LENGTH: 1893
<212> TYPE: DNA
<213> ORGANISM: Aspergillus oryzae
<220> FEATURE:
<221> NAME/KEY: exon
<222> LOCATION: (1001)..(1350)
<220> FEATURE:
<221> NAME/KEY: exon
<222> LOCATION: (1461)..(1590)
```

<400> SEQUENCE: 6

```
atttatgcgc gatttatatg ctgtatcagg cgcccggatg gctttggcag tagccgacgg      60
cagacgacgg tgaatggaat gcaaggaaga gggggattta gcactcactc ttcacaaagt     120
tcaccacgac gctcaagagc cggcgcaaat gatcgcaggt gcggcttggg atgagcgaat     180
gctgaaacac tcctcagaca cggggtcgaa cgagaggggg gattgaggag atggtatcca     240
ggatggagtg gtggaggaag aagaggtgaa agtcggaagt aatttataaa ggctgcgatt     300
ccgcgcgatt cccattactc cacgccaagc ctagattgcc tctttcggaa tggtctccta     360
tcgacctcta agcaaaaacg gtaagaaatg cagaatctc tgcctgcccc cgagctgttt      420
ctccggttcc gatctatgtt ctacatctat acatcaagca gacctcacca atatcctcaa     480
agggaagcag tgcctattat gctctattct ctaatgatta tctggcatta gccttgttga     540
ttggaatgct ccgccaatgg accagactaa agagtatgac tcaggctaaa agtcttcgct     600
acaatccaag gcttgctgga atcagtcgcg tttgtggtca agctggtaat ccaatggact     660
ggagcatgta atatttgggt cagcggggtg tgggggatta gcgggctac actagggcat      720
gtcatcactg cgatgcgttg acgtctacgc caggcaagaa agactgagat cattttcaca     780
taggtagcat ctgaccacaa atagaaagag cattaggctc tctctctctc tctctctctc     840
tctctctctc tctctctatg ttccagttcc acaagctctt atcagtatat cgtatacggc     900
tctcatacgt ctatatatca ttcttggggt gctacaagct tctatcttct atttgtgctt     960
gacaagccaa cccccaactc tctataaccc ctataacgca atg aag gct aac agc    1015
                                               Met Lys Ala Asn Ser
                                                 1               5 ttt ctc att gcc ctc ctc cca acc gcc cta gcc atc ccc ctc ccc aca    1063
Phe Leu Ile Ala Leu Leu Pro Thr Ala Leu Ala Ile Pro Leu Pro Thr
         10                  15                  20 cca aat gaa ggc gct aca agc ctc tca gaa agc cag cgc ctc cag tct    1111
Pro Asn Glu Gly Ala Thr Ser Leu Ser Glu Ser Gln Arg Leu Gln Ser
     25                  30                  35 atc acc gac gag ctt atg ttc ggc ctc gag ctg ccc gac ttc aca gct    1159
Ile Thr Asp Glu Leu Met Phe Gly Leu Glu Leu Pro Asp Phe Thr Ala
 40                  45                  50 cgc aga gag gca aac gac cct cct cag tta gac tgg tac tct gat ggc    1207
Arg Arg Glu Ala Asn Asp Pro Pro Gln Leu Asp Trp Tyr Ser Asp Gly
 55                  60                  65 tgc aca agg gct ccg agt aac cct ctc gga ttc ccc ttt caa agg gcg    1255
Cys Thr Arg Ala Pro Ser Asn Pro Leu Gly Phe Pro Phe Gln Arg Ala
 70                  75                  80                  85 tgt gaa cgc cat gac ttc ggt tac cag aac tac cga ata caa ggg cgc    1303
Cys Glu Arg His Asp Phe Gly Tyr Gln Asn Tyr Arg Ile Gln Gly Arg
         90                  95                 100 ttc acc aag gcc gca aaa gcg cag ata gat ctt aga ttc aaa gaa ga     1350
Phe Thr Lys Ala Ala Lys Ala Gln Ile Asp Leu Arg Phe Lys Glu Asp
        105                 110                 115 gtatgatttc cctttcgttc cttccttctc ccctggaatc tgcttctgtt gattcttatg    1410
gcagttggat attgagagtc tggaggactg acgtttgatt cactgtttag t ctt tac    1467
                                                        Leu Tyr tat caa tgt gaa tta gga cgc gct gtc gga att tgc aag aag ttg gct    1515
Tyr Gln Cys Glu Leu Gly Arg Ala Val Gly Ile Cys Lys Lys Leu Ala
120                 125                 130                 135 cgg ttg tac tac cgt gct tcg ggg cgg cat ggt ggt aaa gat gca gcg    1563
Arg Leu Tyr Tyr Arg Ala Ser Gly Arg His Gly Gly Lys Asp Ala Ala
            140                 145                 150
```

```
aag aga agg gag ttg gat gaa ctt ctt taggtatagg tgcaaaagac      1610
Lys Arg Arg Glu Leu Asp Glu Leu Leu
            155                 160 gcccagtaaa ggggagtcac cacctttgtt aataacatga tacatatatg agaccttgag    1670
tggcaacgga ccacgaagtc tgacctgcat tataagacac aatcttaccc tgaacaacaa    1730
cagatagatt cagagatttt gcataacatg ttgacggatt aaatgtacta ctgtccaggg    1790
ttgtatctat cacaagctag cataaccatc tgaatattgt tgtccagatc acccagatga    1850
ggtacttatt cttccacgta acacttcttg cgtatggatt tca                    1893

<210> SEQ ID NO 7
<211> LENGTH: 482
<212> TYPE: DNA
<213> ORGANISM: Aspergillus oryzae

<400> SEQUENCE: 7
atgaaggcta acagctttct cattgccctc ctcccaaccg ccctagccat ccccctcccc     60
acaccaaatg aaggcgctac aagcctctca gaaagccagc gcctccagtc tatcaccgac    120
gagcttatgt tcggcctcga gctgcccgac ttcacagctc gcagagaggc aaacgaccct    180
cctcagttag actggtactc tgatggctgc acaaggcctc gagtaaccc tctcggattc    240 ccctttcaaa gggcgtgtga cgccatgac ttcggttacc agaactaccg aatacaaggg    300
cgcttcacca aggccgcaaa agcgcagata gatcttagat tcaaagaaga ctttactatc    360
aatgtgaatt aggacgcgct gtcggaattt gcaagaagtt ggctcggttg tactaccgtg    420
cttcggggcg gcatggtggt aaagatgcag cgaagagaag ggagttggat gaacttcttt    480
ag                                                                   482

<210> SEQ ID NO 8
<211> LENGTH: 1782
<212> TYPE: DNA
<213> ORGANISM: Aspergillus oryzae

<400> SEQUENCE: 8
atttatgcgc gatttatatg ctgtatcagg cgcccggatg gctttggcag tagccgacgg     60
cagacgacgg tgaatggaat gcaaggaaga ggggggattta gcactcactc ttcacaaagt    120
tcaccacgac gctcaagagc cggcgcaaat gatcgcaggt gcggcttggg atgagcgaat    180
gctgaaacac tcctcagaca cggggtcgaa cgagaggggg gattgaggag atggtatcca    240
ggatggagtg gtggaggaag aagaggtgaa agtcggaagt aatttataaa ggctgcgatt    300
ccgcgcgatt cccattactc cacgccaagc ctagattgcc tctttcggaa tggtctccta    360
tcgacctcta agcaaaaacg gtaagaaatg cagaatctc tgcctgcccc cgagctgttt    420
ctccggttcc gatctatgtt ctacatctat acatcaagca gacctcacca atatcctcaa    480
agggaagcag tgcctattat gctctattct ctaatgatta tctggcatta gccttgttga    540
ttggaatgct ccgccaatgg accagactaa agagtatgac tcaggctaaa agtcttcgct    600
acaatccaag gcttgctgga atcagtcgcg tttgtggtca agctggtaat ccaatggact    660
ggagcatgta atatttgggt cagcggggtg tggggatta gcgggctac actagggcat    720 gtcatcactg cgatgcgttg acgtctacgc caggcaagaa agactgagat cattttcaca    780
taggtagcat ctgaccacaa atagaaagag cattaggctc tctctctctc tctctctctc    840
tctctctctc tctctctatg ttccagttcc acaagctctt atcagtatat cgtatacggc    900
```

```
tctcatacgt ctatatatca ttcttggggt gctacaagct tctatcttct atttgtgctt      960
gacaagccaa cccccaactc tctataaccc ctataacgca atgaaggcta acagctttct     1020
cattgccctc ctcccaaccg ccctagccat ccccctcccc acaccaaatg aaggcgctac     1080
aagcctctca gaaagccagc gcctccagtc tatcaccgac gagcttatgt tcggcctcga     1140
gctgcccgac ttcacagctc gcagagaggc aaacgaccct cctcagttag actggtactc     1200
tgatggctgc acaagggctc cgagtaaccc tctcggattc ccctttcaaa gggcgtgtga     1260
acgccatgac ttcggttacc agaactaccg aatacaaggg cgcttcacca aggccgcaaa     1320
agcgcagata gatcttagat tcaaagaaga ctttactatc aatgtgaatt aggacgcgct     1380
gtcggaattt gcaagaagtt ggctcggttg tactaccgtg cttcggggcg catggtggt      1440 aaagatgcag cgaagagaag ggagttggat gaacttcttt aggtataggt gcaaaagacg     1500
cccagtaaag gggagtcacc acctttgtta ataacatgat acatatatga gaccttgagt     1560
ggcaacggac cacgaagtct gacctgcatt ataagacaca atcttaccct gaacaacaac     1620
agatagattc agagattttg cataacatgt tgacggatta aatgtactac tgtccagggt     1680
tgtatctatc acaagctagc ataaccatct gaatattgtt gtccagatca cccagatgag     1740
gtacttattc ttccacgtaa cacttcttgc gtatggattt ca                        1782
```

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
cacggaattc atgaagaaca tcttcgttgc                                       30

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
cagcgaattc ctacaggttt tcaatatcgt                                       30

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
cacggaattc atgaaggcta acagctttct                                       30

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
cagcgaattc tcaacagaag cagattccag                                       30

KOJI MOLD-ORIGIN PHOSPHOLIPASE $A_2$

This application is a divisional application of U.S. application Ser. No. 10/547,708, filed Sep. 2, 2005 which is a National Stage of PCT/JP04/02566 filed on Mar. 2, 2004 which claims priority on JP 2003-057565, filed on Mar. 4, 2003, which is hereby incorporated by reference herein in its entirety as if fully set forth herein.

TECHNICAL FIELD

The present invention relates to phospholipase $A_2$ derived from *Aspergillus* and a DNA encoding the same, and uses thereof.

BACKGROUND ART

Among filamentous fungi, in particular, *Aspergillus* including *Aspergillus oryzae* (yellow *Aspergillus*) etc. has been traditionally used in brewing industry in Japan for producing sake, bean paste, soy sauce, mirin, and the like, and directly eaten. *Aspergillus* is a safe source of genes listed up in GRAS (Generally Recognized as Safe) by US FDA (Food and drug Administration).

Therefore, in the safety test such as a chronic toxicity test required when genes derived from general fungi are used for foods, etc., in the case of genes derived from general fungi, the cost is about 1 billion yen. On the other hand, in the case of genes that are the above-mentioned GRAS genes, it is advantageous that the cost can be reduced to about one-third of the cost and further that it takes a shorter time to conduct the test as compared with the case of general genes.

Thus, filamentous fungi, in particular, *Aspergillus* could provide a source of genes with a high utility value from the safe and economical viewpoint.

Therefore, by clarifying information on the genome DNA of these fungi and clarifying the functions of genes encoded thereby, it is possible to provide an effective using method of safe gene resources, for example, production of materials with the use of biotechnology, in food industry; and to provide useful information for screening various kinds of genes in the field of agricultural chemicals and medicine.

Furthermore, it would provide a useful tool for analyzing genome information of grain contamination fungi such as closely-related species including, for example, *Aspergillus flavus*, *Aspergillus fumigatus*, etc. and human-infecting bacteria.

As a result of investigation under the above-mentioned circumstances, the present inventors have succeeded in analyzing the genome of *Aspergillus oryzae*, that is, a kind of *Aspergillus* and have determined the base sequence thereof (and an amino acid sequence encoded by the base sequence) and various functions, etc. Based on such results, the present inventors disclosed various DNAs derived from *Aspergillus oryzae*, as well as a primer set for amplifying a gene of filamentous fungi in GRAS grade including a nucleotide sequence prepared by these DNAs and a probe for detecting genes of filamentous fungi, etc. in the prior patent application (Japanese Patent Application No. 2001-403261).

The present inventors have conducted a further investigation based on the resultant genome information on *Aspergillus*. That is to say, the present inventors paid attention to phospholipase $A_2$ and identified a sequence encoding phospholipase $A_2$ from the resultant base sequences. The present inventors have also tried to identify an amino acid sequence of a protein encoded by the sequence. Note here that phospholipase $A_2$ is an enzyme for hydrolyzing the ester bond at the 2 position of glycerophospholipid so as to separate between fatty acid and lysophospholipid. The presence of phospholipase $A_2$ derived from animals has been traditionally known and such phospholipase $A_2$ has been widely applied in food industry including manufacture of lysolecithin as an emulsifying agent (see, for example, Japanese Patent Unexamined Publication No. H10-042884), a degumming step of fats and oils (see, for example, Industrial Enzymology 2nd ed., p 299-300 (1996)), breadmaking (see, for example, Japanese Patent Unexamined No. S60-2135), functional phospholipid (see, for example, Oleo Science Vol. 2, No. 1 (2002)), and the like. Furthermore, it can be used for development of anti-inflammatory agents, and therapeutic agents for septicemia, rheumatism, asthma, ischemic disease, ischemic reperfusion disorder, and the like. Recently, however, enzymes derived from animals have been tended to be avoided by consumers and food manufacturing companies due to their origins. Enzymes derived from microorganisms that are regarded as being safer have been demanded. In recent years, phospholipase $A_2$ derived from microorganism has been studied, an enzyme of *Streptomyces violaceoruber* that is a kind of *Streptomyces* has been found (see Japanese Patent Unexamined Publication No. 6-327468). In more recent years, an enzyme derived from *Tuber borchii* that is a kind of filamentous fungi (see Soragni et al., The EMBO Journal, 20 (18) 5079-5090 (2001)), and an enzyme derived from filamentous fungi of *Helicosporium* sp. (Wakatsuki et al., Biochin. Biophys. Acta 1522, 74, (2001)) have been reported. However, these microorganisms have never been used for foods and therefore, enzymes derived from safer fungi have been demanded.

It is therefore an object of the present invention to provide phospholipase $A_2$ derived from *Aspergillus* and DNA encoding phospholipase $A_2$ as well as a method for producing phospholipase $A_2$ derived from *Aspergillus*, and the like.

DISCLOSURE OF THE INVENTION

The present inventors have earnestly investigated, and as a result, succeeded in finding two kinds of sequences (hereinafter, referred to as "spaA gene" and "spaB gene") which have higher homology to phospholipase $A_2$ genes derived from the previously reported microorganism in genome of *Aspergillus*. When expressing two kinds of proteins encoded by the sequences (hereinafter, referred to as "phospholipase $A_2$-spaA" and "phospholipase $A_2$-spaB") by using *Escherichia coli* and *Aspergillus* as a host, both proteins showed the phospholipase $A_2$ activity. From the result, it was experimentally confirmed that the two sequences encoded phospholipase $A_2$. On the other hand, the present inventors have succeeded in identifying the coding region in the two kinds of sequences and have found that two kinds of proteins encoded by the sequences have novel amino acid sequences. Thus, the present inventors succeeded in identifying phospholipase $A_2$ gene derived from *Aspergillus* and the amino acid sequence thereof for the first time.

The present invention was completed based on the above-mentioned results and includes the following configurations.

[1] Phospholipase $A_2$ consisting of a protein described in the following (a) or (b):
  (a) a protein having an amino acid sequence set forth in SEQ ID NO: 1; or
  (b) a protein having an amino acid sequence obtained by modifying a part of the amino acid sequence set forth in SEQ ID NO: 1, and functioning as phospholipase $A_2$.

[2] Phospholipase $A_2$ consisting of a protein described in the following (c) or (d):
(c) a protein having an amino acid sequence set forth in SEQ ID NO: 2; or
(d) a protein having an amino acid sequence obtained by modifying a part of the amino acid sequence set forth in SEQ ID NO: 2, and functioning as phospholipase $A_2$.

[3] A DNA described in the following (A) or (B):
(A) a DNA encoding phospholipase $A_2$ described in [1]; or
(B) a DNA which hybridizes under stringent conditions to the DNA described in (A) and encodes a protein functioning as phospholipase $A_2$.

[4] A DNA described in the following (C) or (D):
(C) a DNA encoding phospholipase $A_2$ described in [2]; or
(D) a DNA which hybridizes under stringent conditions to the DNA described in (C) and encodes a protein functioning as phospholipase $A_2$.

[5] A DNA having any one of the following sequences (i) to (vi):
(i) a base sequence of SEQ ID NO: 3;
(ii) a base sequence of SEQ ID NO: 4;
(iii) a base sequence of SEQ ID NO: 5;
(iv) a base sequence of SEQ ID NO: 6;
(v) a base sequence of SEQ ID NO: 7; and
(vi) a base sequence of SEQ ID NO: 8.

[6] A vector carrying the DNA described in any of [3] to [5].

[7] Filamentous fungi into which the DNA described in any of [3] to [5] is exogenously introduced.

[8] A method for producing phospholipase $A_2$, the method comprising the following steps (1) and (2):
(1) a step of culturing the filamentous fungi described in [7] under conditions where a protein encoded by the DNA can be produced; and
(2) a step of recovering the produced protein.

The "DNA" of the present invention is not limited to a double strand DNA but is intended to include a single strand DNA (sense chain and antisense chain) constituting the double strand DNA. Furthermore, the DNA of the present invention includes a DNA having an arbitrary base sequence considering the degeneracy of codons. Furthermore, the form of the DNA is not limited and may include a cDNA, a genome DNA and a synthetic DNA.

The "DNA encoding a protein" of the present invention is a DNA from which a protein is obtained when it is expressed. The "DNA" includes not only a DNA having a base sequence corresponding to an amino acid sequence of the protein but also a DNA obtained by adding a sequence that does not encode an amino acid sequence to the DNA having a base sequence corresponding to an amino acid sequence of the protein (examples of the latter DNA includes a DNA including one or a plurality of introns).

The "phospholipase $A_2$ derived from *Aspergillus*" of the present invention includes phospholipase $A_2$ prepared by using *Aspergillus* as a starting material or phospholipase $A_2$ prepared by using information (amino acid sequence or DNA sequence) of phospholipase $A_2$ carried by *Aspergillus* in the process of obtaining phospholipase $A_2$. Examples of such phospholipase $A_2$ include not only phospholipase $A_2$ prepared from *Aspergillus* by using a physical technique, a biochemical technique and the like, but also phospholipase $A_2$ prepared by a genetic engineering technique using an amino acid sequence or a DNA sequence of the phospholipase $A_2$ disclosed in the present invention.

Figure 1:
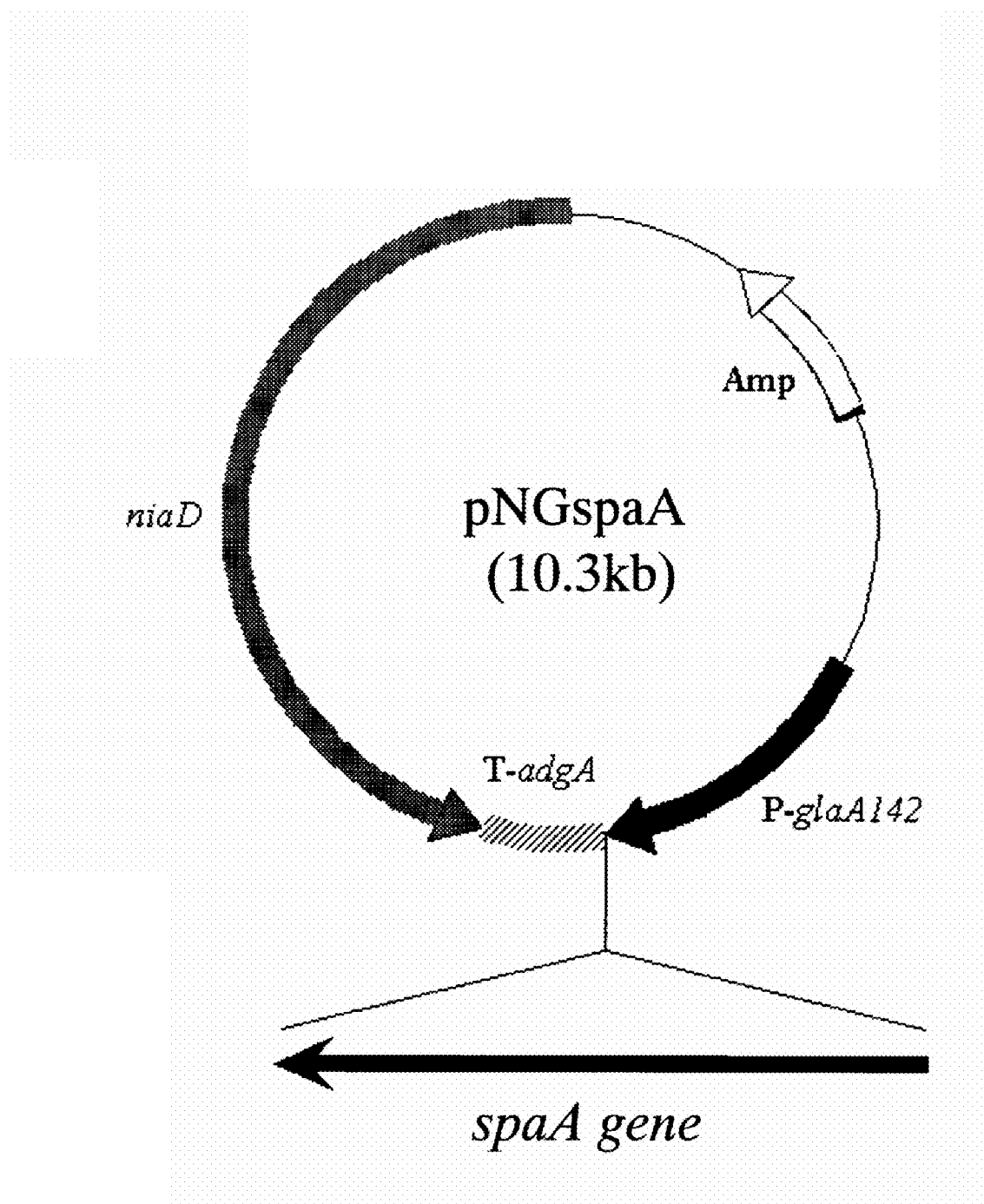
FIG. 1 is a schematic view showing a configuration of an expression vector pNGspaA.

BEST MODE FOR CARRYING OUT THE INVENTION (Protein)

The first aspect of the present invention relates to phospholipase $A_2$ derived from *Aspergillus*. Phospholipase $A_2$ provided in the present invention includes a protein having, for example, an amino acid sequence set forth in SEQ ID NO: 1 or SEQ ID NO: 2. As shown in the below-mentioned Examples, it has been confirmed that the protein actually exhibits a phospholipase $A_2$ activity in the expression system using filamentous fungi.

Herein, in general, in a case where a part of the amino acid sequence of a protein is modified, a protein after modification has the same function as that of a protein before modification. That is to say, modification of the amino acid sequence may not substantially affect the function of the protein and the function before modification may be maintained after modification. Taking this fact into consideration, a protein obtained by modifying a part of the amino acid sequence (SEQ ID NOs: 1 and 2) of the protein having the above-mentioned phospholipase $A_2$ activity (hereinafter, referred to as a "modified protein") may constitute the phospholipase $A_2$ (protein) of the present invention as long as the function as phospholipase $A_2$ is maintained. In other words, as long as the function as phospholipase $A_2$ is maintained, a part of the amino acid sequence is allowed to be modified. Note here that it is preferable that the phospholipase $A_2$ activity is not decreased as a result of modification, however, somewhat fluctuation (increase or decrease) of the phospholipase $A_2$ activity is allowed.

The phrase "a part of an amino acid sequence is modified" herein means that one or a plurality of amino acids in the amino acid sequence are deleted, substituted, added and/or inserted. The position of the modification (mutation) of the amino acid sequence is not particularly limited as long as the phospholipase $A_2$ activity is maintained. Furthermore, modification may be conducted at a plurality of positions. The number of amino acids to be modified may be, for example, the number corresponding to 10% or less of the entire amino acids, preferably the number corresponding to 5% or less of the entire amino acids, and further preferably the number corresponding to 1% or less of the entire amino acids. The above-mentioned modified protein can be formed by a genetic engineering technique, for example, by preparing a nucleic acid fragment which has a sequence obtained by modifying a base sequence coding the amino acid sequence of SEQ ID NO: 1 or 2 and makes this fragment to express in a suitable expressing system.

Among the protein (including modified protein) of the present invention, the protein of natural *Aspergillus* can be prepared by operations such as extraction and purification from the *Aspergillus*. Furthermore, the protein (including modified protein) of the present invention can be prepared by the genetic engineering technique based on information of phospholipase $A_2$ disclosed herein. For example, a DNA encoding the protein of the present invention is used so as to transform an appropriate host cell and proteins expressed in the transformant are collected, to thus prepare the proteins of the present invention. The collected proteins are appropriately purified in accordance with the purposes. In a case where a protein is prepared as a recombinant protein, various modifications can be conducted. For example, when DNA encoding the protein of the present invention and other appropriate DNA are inserted into the same vector and the vector is used so as to produce a recombinant protein, a recombinant protein in which the protein of the present invention is linked to other peptide or protein can be obtained. Furthermore, modification may be carried out so that addition of a sugar chain and/or lipid or processing of N terminal or C terminal occur. With such a modification, it is possible to simplify extraction and purification of a recombinant protein, or to add the biological functions thereto, and the like.

(DNA Encoding Phospholipase $A_2$)

According to a second aspect of the present invention, a DNA encoding phospholipase $A_2$ derived from *Aspergillus* is provided. Specific examples of such a DNA can include a DNA having a base sequence of SEQ ID NO: 3 or SEQ ID NO: 4 or a DNA having a base sequence of SEQ ID NO: 7. The sequence of SEQ ID NO: 3 or SEQ ID NO: 4 is a sequence derived from genome DNA (a phospholipase $A_2$ gene) encoding phospholipase $A_2$. The sequence of SEQ ID NO: 7 is a sequence obtained by excluding the intron region from the sequence of SEQ ID NO: 4. Another specific example of the DNA of the present invention can include a DNA having a base sequence of SEQ ID NO: 5, 6 or 8. The base sequence of SEQ ID NO: 5 is a sequence of DNA including a phospholipase $A_2$ gene set force in SEQ ID NO: 3 and its putative promoter and terminator regions. Similarly, the base sequence of SEQ ID NO: 6 is a sequence of DNA including a phospholipase $A_2$ gene set force in SEQ ID NO: 4 and its putative promoter and terminator regions. Furthermore, the base sequence of SEQ ID NO: 8 is a sequence of DNA including a DNA set force in SEQ ID NO: 7 (DNA that is a phospholipase $A_2$ gene from which an intron region is excluded) and its putative promoter and terminator regions. Since these DNAs have ideal combination of a promoter and a terminator and a structural gene, if phospholipase $A_2$ is produced by using these DNAs, excellent gene expression can be expected. Therefore, an efficient production system of phospholipase $A_2$ can be constructed.

The above-mentioned DNAs of the present invention can be prepared by appropriately using a probe, a primer, etc. capable of hybridizing specifically to a gene encoding the phospholipase $A_2$ of the present invention (for example, a DNA having a base sequence of SEQ ID NO: 3 or 4) from an appropriate filamentous fungi genome DNA library or a cDNA library, or a cell extract of filamentous fungi. Note here that a production method of the genome DNA library of filamentous fungi or the cDNA library can be referred to, for example, Molecular Cloning, Third Edition, Cold Spring Harbor Laboratory Press, New York.

Specifically, the DNA of the present invention can be prepared by, for example, the following procedures. First of all, filamentous fungi which are expected to carry a targeted DNA are cultured for a predetermined period of time. And then filtration is conducted so as to collect fungi. The collected fungi are washed and then freeze-dried. Then, the fungus bodies are ground with the use of a mortar, etc. and an appropriate amount of extraction buffer solution (for example, SDS-containing Tris-HCl buffer solution) is added thereto so as to obtain an extraction solution. Then, a genome DNA is extracted and purified by phenol extraction, ethanol precipitation, and the like. By using the thus obtained genome DNA as a template, the PCR method is conducted by using a primer specific to the targeted DNA, so that the targeted DNA can be obtained as an amplification product.

The DNA of the present invention can be also prepared by using an appropriate filamentous fungi genome DNA library or cDNA library if it is available. In accordance with the kinds of libraries to be used, a plaque hybridization technique or a colony hybridization method can be used (see, for example, Molecular Cloning, Third Edition, Cold Spring Harbor Laboratory Press, New York). For example, in a case of the library constructed by using a plasmid, a colony hybridization method is used. For selecting a clone carrying the targeted DNA, a probe having a sequence specific to the DNA of the present invention is used. When the targeted clone is selected, PCR method, etc. using the DNA carried by this clone as a template is conducted by using a primer specific to the sequence of the targeted DNA, so that the DNA of the present invention can be obtained as an amplification product.

The DNA carried by the obtained clone can be subcloned into an appropriate vector so as to be used followingly. Thereby, for example, it is possible to construct a recombinant vector for transformation or a plasmid suitable for decoding a base sequence.

Herein, in general, in a case where a part of a DNA encoding a protein is modified, a protein encoded by the modified DNA may sometimes have the equivalent function to that of a protein encoded by the DNA before modified. That is to say, modification of the DNA sequence does not substantially affect the function of the protein encoded by the DNA and sometimes may maintain the function of the encoded protein before and after modification. Taking this fact into consideration, a DNA having a base sequence obtained by modifying a part of the above-mentioned DNA of the present invention (hereinafter, the DNA will be also referred to as "modified DNA") can constitute the DNA of the present invention as long as the protein encoded by the DNA has a function as a phospholipase $A_2$. In other words, as long as the function as phospholipase $A_2$ of the encoded protein is maintained, a part of the sequence is allowed to be modified. Note here that it is preferable that the phospholipase $A_2$ activity is not decreased as a result of modification, however, somewhat fluctuation (increase or decrease) of the phospholipase $A_2$ activity is allowed.

Herein, "a part of DNA . . . is modified" typically denotes that one or a plurality of bases are substituted, deleted, inserted, or added in the base sequence before modification. Such modification may be occurred in a plurality of sites. "A plurality" herein differs depending upon the position to be modified or kinds of modifications, but the plurality of numbers is, for example, 2 to 100, preferably 2 to 50 and more preferably 2 to 10. The above-mentioned modified DNA can be obtained by, for example, a treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York); random mutagenesis (Molecular Cloning, Third Edition, Chapter 13, Cold Spring Harbor Laboratory Press, New York), and the like. Furthermore, the modified DNA can be obtained by a well-known method using a mutation treatment, for example, treating filamentous fungi carrying a phospholipase $A_2$ gene with ultraviolet ray, followed by isolating the modified gene.

Note here that the mutation by substitution, deletion, insertion, insertion, addition, or inversion, etc. of the bases as mentioned above may include naturally occurring mutation based on the individual difference, difference in species or genera of microorganism carrying phospholipase $A_2$, etc.

An example of a method for preparing the modified DNA can include a method of including: extracting a genome (chromosomal) DNA from naturally occurring *Aspergillus* (*Aspergillus oryzae*) carrying a modified DNA; treating the extracted DNA with an appropriate restriction enzyme; and then selecting and isolating a DNA that hybridizes under stringent conditions in a screening using a DNA of the present invention (for example, DNA having a sequence of SEQ ID NO: 3 or 4) or a part thereof as a probe. When a genome (chromosomal) DNA library including a clone carrying a modified DNA can be used, the DNA can be obtained by screening using the DNA of the present invention (for example, a DNA having a sequence of SEQ ID NO: 3) or a part thereof as a probe under stringent conditions.

The DNA of the present invention may include a DNA that hybridizes to the DNA of the present invention (for example, a DNA having a sequence set forth in SEQ ID NO: 3 or 4, or a DNA obtained by modifying the DNA as mentioned above) under stringent conditions and encodes a protein that functions as phospholipase $A_2$. The "stringent conditions" herein denote a condition in which a so-called specific hybrid is formed and a non-specific hybrid is not formed. The stringent conditions fluctuate depending upon the length of the sequence or kinds of constituting bases. However, an example of the stringent conditions includes a condition in which a DNA is incubated in a hybridization solution (50% formaldehyde, 10×SSC (0.15 M NaCl, 15 mM sodium citrate, pH 7.0), 5×Denhardt solution, 1% SDS, 10% dextran sulfate, 10 µg ml denatured salmon sperm DNA, 50 mM phosphate buffer (pH7.5)) at 42° C., followed by washing with 0.1×SSC and 0.1% SDS at 68° C. A more preferable example of the stringent conditions can include a condition using a hybridization solution (50% formaldehyde, 5×SSC (0.15 M NaCl, 15 mM sodium citrate, pH 7.0), 1×Denhardt solution, 1% SDS, 10% dextran sulfate, 10 µg/ml denatured salmon sperm DNA, 50 mM phosphate buffer (pH 7.5)).

(Vector)

According to another aspect of the present invention, a vector carrying the DNA of the present invention (including a modified DNA) is provided. Such a vector is prepared by introducing the DNA of the present invention into an existing vector or a vector obtained by adding modification to the existing vector. Any vectors may be used as a starting material in principle as long as they can carry the DNA of the present invention, however, an appropriate vector can be selected in accordance with the purpose of use (cloning, expression of polypeptide), while considering the kinds of host cells. The introduction of the DNA of the present invention into a vector can be conducted by a well-known method using a restriction enzyme and DNA ligase (see, Molecular Cloning, Third Edition, 1.84, Cold Spring Harbor Laboratory Press, New York).

Note here that when a DNA that includes also a promoter region (for example, a DNA having a sequence of any of SEQ ID NOs: 5, 6 and 8) is constructed, a recombinant vector may be constructed by incorporating a separately prepared promoter region and other regions of the DNA into a vector. In such a case, as long as a promoter function is appropriately exhibited, other sequences may be intervened between both regions (the promoter region and the other regions) in the vector. Furthermore, a vector carrying the promoter region may be constructed firstly and then ligated to the other regions.

Typically, a vector for transformation contains a phospholipase $A_2$ gene (for example, a DNA having a sequence of SEQ ID NO: 3), a promoter and a terminator. In order to achieve an appropriate transcription of a structural gene by a promoter, a promoter, a gene of phospholipase $A_2$ and a terminator are arranged successively from the upper stream toward the lower stream. A selection marker, a sequence having an enhancer function, and a sequence encoding a signal peptide may be contained in the vector.

(Transformant)

The vector for transformation can be used for transforming filamentous fungi. That is to say, by using the above-mentioned vector for transformation, a preparation method of the transformed filamentous fungi can be constructed. With such a preparation method, filamentous fungi into which the DNA of the present invention is exogeneously introduced can be obtained. The thus obtained transformed filamentous fungi can be used for production of phospholipase $A_2$. Specifically, by culturing transformed filamentous fungi into which the DNA of the present invention is exogeneously introduced under conditions where a protein (phospholipase $A_2$) encoded by the DNA, phospholipase $A_2$ can be produced. Any appropriate culture media can be used in accordance with a host to be used. For example, various kinds of commercially available culture media or culture media to which ingredient necessary for growth, selection and promotion of expression of protein for example, arginine, uridine, and the like are added can be used.

From the culture medium solution or fungus bodies after being cultured for a predetermined period of time, targeted protein (phospholipase $A_2$) can be collected. When the proteins are produced outside fungus bodies, the proteins can be collected from the culture medium solution. In other case, the proteins can be collected from fungus bodies. When the proteins are collected from the culture medium solution, for example, after insolubles are removed by filtration and centrifugation of the culture supernatant, the targeted proteins can be obtained by isolation and purification by combining salting out such as ammonium sulfate precipitation, etc., dialysis, various chromatography, and the like. On the other hand, when the proteins can be collected from the fungus bodies, for example, the targeted proteins can be obtained by isolation and purification as mentioned above after the fungus bodies are ground by a pressure treatment, ultrasonic treatment, etc. Note here that after the fungus bodies are collected from a culture medium solution by filtration, centrifugation, etc. in advance, the above-mentioned series of steps (girding of fungus bodies, isolation and purification) may be conducted. Note here that since the phospholipase$A_2$ of the present invention is generally produced outside the fungus bodies, the isolation and purification thereof can be conducted relatively easily.

The kinds of host filamentous fungi to be used for transformation are not particularly limited. Filamentous fungi classified in genera of *Aspergillus* (*Aspergillus oryzae*,

*Aspergillus niger, Aspergillus nidulans, Aspergillus sojae, Aspergillus awamori, Aspergillus kawachii, Aspergillus parasiticus, Aspergillus flavus, Aspergillus nomius, Aspergillus fumigatus*, and the like), *Penicillium, Trichoderma, Rhizopus, Mucor, Fusarium* or the like, can be used. Preferably, filamentous fungi in *Aspergillus* genera is used. Among them, *Aspergillus oryzae* or *Aspergillus niger* is preferably used from the viewpoint of safety.

The vector for transformation can be introduced (transformed) into the host filamentous fungi by a well-known method. For example, it can be conducted by a method by Turner et al. using, for example, fungus body as a protoplast (see Gene, 36, 321-331 (1985)). Besides, a method by Gomi et al. (Agric. Biol. Chem., 51, 323-328 (1987)) may be employed.

EXAMPLE

Hereinafter, the present invention will be described in more detail with reference to Examples, but the present invention is not necessarily limited thereto. Note here that various kinds of genetic engineering techniques in Examples were conducted in accordance with the method described in Current protocols in molecular biology (edited by Frederick M. Ausubel et al., 1987) mentioned above.

Example 1

Production Method of Whole-genome Shotgun Library

1. Preparation of Insert Side
(1) Obtaining of Chromosomal DNA

Spores of filamentous fungi, *Aspergillus oryzae* RIB-40 strain (ATCC 42149) were inoculated in a YPD culture medium (0.5% yeast extract, 1% peptone and 2% glucose) and cultured with shaking overnight at 30° C. Thereafter, a genome DNA was extracted in accordance with a method by Iimura (Argric. Biol. Chem. 323-328, 51 (1987)). In order to exclude a mitochondrial DNA mixed in the genome DNA, purification by cesium chloride ultracentrifugation was carried out so as to obtain only a chromosomal DNA in accordance with the method by Watson et al. (Methods Enzymol. 57-75 118 (1986)).

(2) Fragmentation of Chromosomal DNA

The obtained pure chromosomal DNA was placed in a DNA fragmentation device HydroShear (TOMY SEIKO Co., Ltd.) so as to form the chromosomal DNA into fragments of about 1-2 kb.

(3) End Treatment of Fragmented DNA

The fragmented chromosomal DNA was treated with BAL31 nuclease (TAKARA) and then the end thereof was blunted by treatment with a Klenow Fragment (TAKARA).

(4) Addition of Adaptor to the End

To both ends of the end-blunted chromosomal DNA fragment, an adaptor consisting of (P)5'-CGAGAGCGGCCGC-TAC-3' and (P)5'-GTAGCGGCCGCTC-3' was ligated by using T4 DNA Ligase (TAKARA).

2. Transformation

After pUC19 was cut with a restriction enzyme SalI (TAKARA), dT was inserted into the part cut with SalI by using Taq DNA polymerase (Roche Diagnostics K.K.). The thus produced plasmid was dephospholylated by a treatment using Alkaline Phosphatase (TAKARA) and used as a vector. The vector and the above produced chromosomal DNA fragment were ligated to each other by using T4 DNA Ligase and transformation was conducted by electroporation in *Escherichia coli* DH10B (Gibco).

3. Determination of Base Sequence

The full length of the insertion fragment of the plasmid DNA including a site where a sequencing primer was annealed was amplified by culturing *Escherichia coli* transformant in a 2×YP medium at 37° C. for 10 hours so as to collect fungi, followed by heat-treating in sterile water at 99° C. for 10 minutes so as to obtain a supernatant; and carrying out PCR using the supernatant 30 cycles of reactions at 98° C. for 20 seconds and at 68° C. for 2 minutes. The obtained DNA fragment was used as template for Sangaer method so as to carry out a sequence reaction by using M13 universal primer or M13 reverse primer and PRISM Dye-Terminator Sequencing Kit (Perkin Elmer) in accordance with the instruction attached to the kit. Sequence reaction product was subjected to gel filtration etc. so as to remove unreacted Dye-terminator and thereafter the base sequence of DNA fragment was decoded by using 3700 DNA Sequencer (Perkin Elmer). Waveform data output from the 3700 DNA Sequencer was analyzed again by using Phred (Phil Green), vector and adaptor sequences were removed, followed by assembling by SPS Phrap (Southwest Parallel Software Inc.) so as to construct Contig sequence of *Aspergillus* genome DNA base sequence.

Example 2

Identification of Gene

Identification of gene from a genome DNA base sequence was conducted by the following technique. In the technique of identifying genes, with respect to the contig sequence of the genome DNA base sequence, the combination of a gene region prediction system GeneDecoder based on algorithm by Kiyoshi Asai et al. (Pacific Symposium on Biocomputing 98, 228-239) and a gene region prediction system ALN based on algorithm (Bioinformatics 2000 16: 190-202) by Osamu Goto was used while considering the homology between sequence information on the previously obtained EST and the amino acid sequence database of the well-known protein. Furthermore, for predicting a tRNA gene, tRNA-scan was used.

<1> "Extraction of BLAST Homologous Gene Candidate Region"

A region having a high homology to the amino acid sequence of the known protein was extracted from the contig sequence of the genome DNA base sequence. The homology of amino acid sequence can be determined by algorithm BLAST by Karlin and Altschul (Proc. Natl. Acad. Sei. USA 87:2264-2268, 1990, Proc. Natl. Acad. Sei. USA 90:5873-5877, 1993). Based on this algorithm, a program called BLASTX was developed (Altschul et al. J. Mol. Biol. 215: 403-410, 1990). When the genome DNA base sequence is translated into the amino acid sequence, a region having high homology can be directly retrieved. The specific technique of these analysis methods is well known (http://www.ncbi.nlm.nih.gov). In this technique, by searching the BLASTX under the conditions that the contig sequence of the genome DNA base sequence is used as a query sequence and that SWISSPROT version 39 (Bairoch, A. & Apweiler, R. Nucleic Acids Res. 28, 45-48 (2000).) and NRaa are used as databases, and then a region having an E-value (i.e., index of homology in BLAST algorithm) of $10^{-30}$ or less is extracted (note here that as the E-value is small, the homology is high). From these regions, BLAST homologous gene candidate regions are extracted by giving high priority to a part having high homology so that the candidate regions are not overlapped with each other.

<2> "Extract of ALN Gene Candidate Region"

Among the BLAST homologous gene candidate regions, a region having homology with respect to 90% or more of the full length of the amino acid sequence of the protein that is a subject of homology is made to be core, and an ALN gene candidate region is extracted by applying a gene region prediction system ALN with respect to the contig sequence. The ALN predicts a gene region by identifying a splice site while aligning the full length of an amino acid sequence of the protein that is a subject of homology with respect to the contig sequence.

<3> "Extraction of GD Homologous Gene Candidate region"

Among the BLAST homologous gene candidate regions, a region having homology with respect to 20% or more and less than 90% of the full length of the amino acid sequence of the protein that is a subject of homology is made to be core, and a GD homologous gene candidate region is extracted by applying a gene region prediction system GeneDecoder with respect to the contig sequence. The GeneDecoder predicts a gene region by integrating E-value of BLASTX and statistic amount of 2 series of codons (index of direction of the protein coding region) and further considering a score by a position-dependent primary Markov Model of the splice site.

<4> "Extraction of EST-GD Gene Candidate Region"

As to a region in which gene expression is confirmed by EST corresponding to the contig sequence, by applying GeneDecoder to the contig sequence in the vicinity of the region, not only a gene region determined by EST sequence but also an entire region of gene is predicted. Thus, an EST-GD gene candidate region is obtained.

<5> "Extraction of General GD Gene Candidate Region"

With respect to the contig sequence that is not included in <1> to <4> mentioned above, by applying GeneDecoder, gene a region is predicted.

<6> Extraction of tRNA Gene Candidate Region"

By applying tRNA-scan to the entire contig sequence, a tRNA gene region candidate region is extracted.

<7> "Integration of Gene Candidate Regions"

By the following procedures, gene candidate regions described in the above <2> to <6> are integrated. Firstly, in the gene candidate regions <2> to <6>, a gene region that is expected to have gene regions which are contradictory to the splice site determined by EST are removed. The rest of the gene candidate regions are integrated while excluding the regions overlapped with each other. At this time, tRNA, ALN homologous gene candidate region, GD homologous gene candidate region, GD-EST gene candidate region, general GD gene candidate region are integrated by giving a higher priority in this order. This integrated gene candidate regions are made to be a set of the prediction genes.

By the above-mentioned procedures, from the viewpoint of homology, a gene having homology over the full length of the well-known protein, a gene having homology to a part of the well-known protein, and a gene having no homology to the well-known protein are ensured to be identified with higher reliability in this order. Furthermore, from the viewpoint of confirmation of expression, a gene whose expression is confirmed by EST and a gene whose expression is not confirmed by EST are identified with reliability in this order. Furthermore, all the candidate genes are ensured that they are not contradictory to the splice site identified by EST.

The technique used employs algorithm that is not allowed to contain a stop codon in a protein encoding region, so that there is little possibility of predicting a false gene as a gene.

As to determination of functions, with respect to the predicted gene region, the database Nraa in BLAST is searched for homology, and the function is determined with a sufficient homology (E-value: $10^{-30}$) as a threshold value.

Example 3

Retrieving for Sequence Encoding Phospholipase $A_2$

Based on DNA sequence of phospholipase $A_2$ gene derived from filamentous fungi of *Helicosporium* sp., BLAST search (Standard protein-protein BLAST: blastp) provided by NCBI was carried out with respect to all DNA sequence of *Aspergillus* genome DNA. As a result, the present inventors succeeded in finding two regions having high homology to phospholipase $A_2$ gene derived from filamentous fungi of *Helicosporium* sp. One of the found regions was a region that had been expected to be a sequence having certain functions in identifying the above-mentioned gene in which the function had not been estimated. Note here that a coding region of the gene (putative phospholipase A2-spaA coding region) is shown in SEQ ID NO: 3. Furthermore, an amino acid sequence encoded by the region is shown in SEQ ID NO: 1.

On the other hand, another region (sequence) was firstly expected to have a translation function and existed in the sequence whose function had not been estimated. Furthermore, this sequence was firstly expected to encode a protein consisting of 624 amino acid residues being utterly different from those of the amino acid sequence identified this time. However, according to this time investigation, it was found that the sequence encoded 160 amino acid sequence (SEQ ID NO: 2) having higher homology to the amino acid sequence of phospholipase $A_2$ derived from filamentous fungi. The base sequence encoding the amino acid sequence is shown in SEQ ID NO: 7 (coding region of putative phospholipase $A_2$-spaB) (a sequence including intron is shown in SEQ ID NO: 4). Note here that such a difference was caused because the intron had not been estimated correctly in the original prediction. Furthermore, by considering the fact that two kinds of phospholipase $A_2$ genes (GenBank database: ACCESSION NO. NCU06650, NCU09423) existed in *Neurospora crassa*, the present inventors predicted that another phospholipase $A_2$ gene other than the aforementioned sequence (SEQ ID NO: 3) existed in a genome sequence of the present invention and investigated based on the prediction. Thus, the present inventors succeeded in finding the amino acid sequence (SEQ ID NO: 2).

For the purpose of analyzing the function of the two regions (sequences) identified as mentioned above, the following various experiments were conducted.

Example 4

Obtaining Genome DNA

*Aspergillus oryzae* RIB-40 strain was cultured at 30° C. for two days by using an Erlenmeyer flask containing 200 ml of DPY culture medium (2% dextrin, 1% polypeptone, 0.5% yeast extract, 0.5% KH2PO$_4$, 0.05% MgSO$_4$-7H$_2$O, pH 5.5). Then, the medium solution was filtrated by using a Buchner funnel and Nutsche suction bottle to obtain fungus bodies. The fungus bodies, which had been frozen with liquid nitrogen, was ground by using a mortar and pestle, added with 20 ml Sol I (50 mM EDTA, 0.5% SDS, 0.1 mg/ml Proteinase K, pH 8.0), and incubated at 50° C. for four hours. Treatment with phenol, treatment with phenol-chloroform and treatment with chloroform were carried out twice, once and once, respectively (centrifugation was carried out at 3,500 rpm, for 15 minutes, at 4° C.). To supernatant, one-tenth amount of 3 M sodium acetate (pH 5.2) and equivalent amount of isopropanol were added and cooled on ice overnight. Centrifugation was carried out at 3,500 rpm for 20 minutes at 4° C., then precipitation was rinsed with 70% ethanol, and then dissolved in TE (10 mM Tris-HCl (pH8.0), 1 mM EDTA) solution. Next, RNase Awas added so as to be 10 μg/ml and incubation was carried out at 37° C. for 30 minutes. Equivalent amount of phenol-chloroform was added and mixed, followed by centrifugation at 3,500 rpm for 20 minutes at 4° C. to recover the upper layer. One-tenth amount of 3M sodium acetate (pH 5.2) and 2.5 times amount of ethanol was added, followed by centrifugation at 3,500 rpm for 20 minutes at 4° C. to obtain precipitation. This was made into a chromosomal DNA solution.

Example 5

Obtaining Phospholipase $A_2$ Gene

Based on the sequence information of genome DNA contig of *Aspergillus* obtained in Example 3, phospholipase $A_2$-spaA and phospholipase $A_2$-spaB genes were cloned using a genome DNA of *Aspergillus* obtained in Example 4 as a template. Primer pair for amplifying a DNA fragment that was expected to be from putative initiation codon to stop codon of respective targeted genes (putative phospholipase $A_2$-spaA and phospholipase $A_2$-spaB genes) was designed as follows.

Primer for Phospholipase $A_2$-spaA Gene:

```
                                     (SEQ ID NO: 9)
Ao1724s:    5'-cagcgaattcATGAAGAACATCTTCGTTGC-3'

(SEQ ID NO: 10)
Ao1724as:   5'-cagcgaattcCTACAGGTTTTCAATATCGT-3'
```

As to phospholipase $A_2$-spaB gene, assuming that in the gene of the present invention, introns corresponding to the similar positions exist by considering the fact that in two kinds of phospholipase $A_2$ genes derived from *Neurospora crassa* (GenBank database: ACCESSION NO. NCU06650, NCU09423), introns are found, respectively, the homology with respect to the amino acid sequence of phospholipase $A_2$ derived from the other microorganism becomes higher. In consideration of this, primer pair for amplifying the phospholipase $A_2$-spaB gene was designed as follows.

Primer for Phospholipase $A_2$-spaB Genes:

```
                                     (SEQ ID NO: 11)
Ao0940s:    5'-cagcgaattcATGAAGGCTAACAGCTTTCT-3'

(SEQ ID NO: 12)
Ao0940as:   5'-gcgcgaattccaaggtctcatatatgtatc-3'
```

Note here that underlines in the above-mentioned four primers show Eco RI recognition sites and capital letters show coding regions of protein, respectively.

By using the above-mentioned primer pairs, PCR was conducted. Note here that the composition of the reaction solution was as follows.
  sterile water: 29.75 μl
  10× Buffer for rTaq DNA Polymerase: 5 μl
  2 mM dNTP solution: 5 μl
  10 pmol/μl Ao1724s or Ao0940s: 2.5 μl
  10 pmol/μl Ao1724 as or Ao0940 as: 2.5 μl
  60 ng/μl RIB40 genome DNA: 5 μl
  5 U/μl rTaq DNA Polymerase (Takara Shuzo Co. Ltd.): 0.25 μl/50 μl The above-mentioned reaction solution was subjected to PCR by using PTC-100 type PCR apparatus (MJ Research) under the following conditions.
(1) Reaction at 94° C. for 1 minute, (2) 30 cycles of reactions at 94° C. for 30 seconds, at 50° C. for 30 seconds and at 72° C. for 2 minutes, and (3) allowed to stand at 4° C.

As a result of PCR, about 670 bp and about 700 bp of DNA fragments were specifically amplified. The amplified DNA fragments were extracted by using GeneCleanIII (BIO 101) after carrying out Agarose gel electrophoresis. The extracted DNA fragment was ligated to pT7-Blue (Novagen) and the base sequence was determined by a conventional method.

Example 6

Analysis of Amino Acid Sequence

The analysis of the base sequences obtained in Example 5 reveled that they were sequences of DNA (SEQ ID NO: 3 and 4) encoding a protein having about 35% to about 55% homology to the previously reported amino acid sequence of phospholipase $A_2$ derived from microorganism. The DNAs were made to be spaA and spaB genes, respectively. A putative phospholipase $A_2$-spaA encoded by spaA gene consisted of full length 222 amino acids, had the molecular weight excluding the signal sequence region (19 amino acids) predicted by SMART (Schultz et al., Proc. Natl. Acad. Sci. USA 95, 5857-5864 (1998); Letunic et al., Nucleic Acids Res. 30, 242-244 (2002); http://smart.embl-heidelberg.de/) of 23.4 kDa, and contained six cysteines. On the other hand, a putative phospholipase $A_2$-spaB encoded by spaB gene consisted of full length 160 amino acids, had the molecular weight excluding the signal sequence region (17 amino acids) predicted by the above-mentioned SMART of 16.4 kDa, and contained four cysteines. Both enzymes had an active center, His-Asp pair sequence, which could be commonly seen in secretion type phospholipase $A_2$.

Example 7

Construction of *Aspergillus* Expression Vector pNGspaA

Next, a plasmid pNGspaA for expressing phospholipase $A_2$-spaA in *Aspergillus* was constructed. Firstly, the phospholipase $A_2$-spaA gene cloned to pT7-Blue obtained in Example was digested with restriction enzymes Hind III and Xba I (Takara Shuzo Co. Ltd.) to obtain about 670 bp DNA fragment as an insert DNA. On the other hand, *Aspergillus* expression vector pNGA142 having niaD gene derived from *Aspergillus* as a selection marker, a modified promoter of a modified type glucoamylase gene derived from *Aspergillus* as a promoter and a terminator of α-glucosidase gene derived from *Aspergillus* as a terminator (Minetoki et al., Appl. Microbiol. Biotechnol., 50, 459-467 (1988)) was digested with Hind III and Xba I (Takara Shuzo Co. Ltd.). Thereafter, dephosphorylation was carried out with the use of Alkaline Phosphatase (Takara Shuzo Co. Ltd.) to obtain a vector DNA. The insert DNA and the vector DNA, which had been prepared as mentioned above, were ligated to each other with the use of Ligation Kit ver.2 (Takara Shuzo Co. Ltd.), thereby transforming *Escherichia coli* DH5α strain competent cell (TOYOBO) to obtain an ampicillin resistant transformant. The plasmid carried by the obtained clone was called pNGspaA and used as an expression vector (see FIG. 1).

Example 8

Construction of *Aspergillus* Expression Vector pNGspaB

Figure 2:
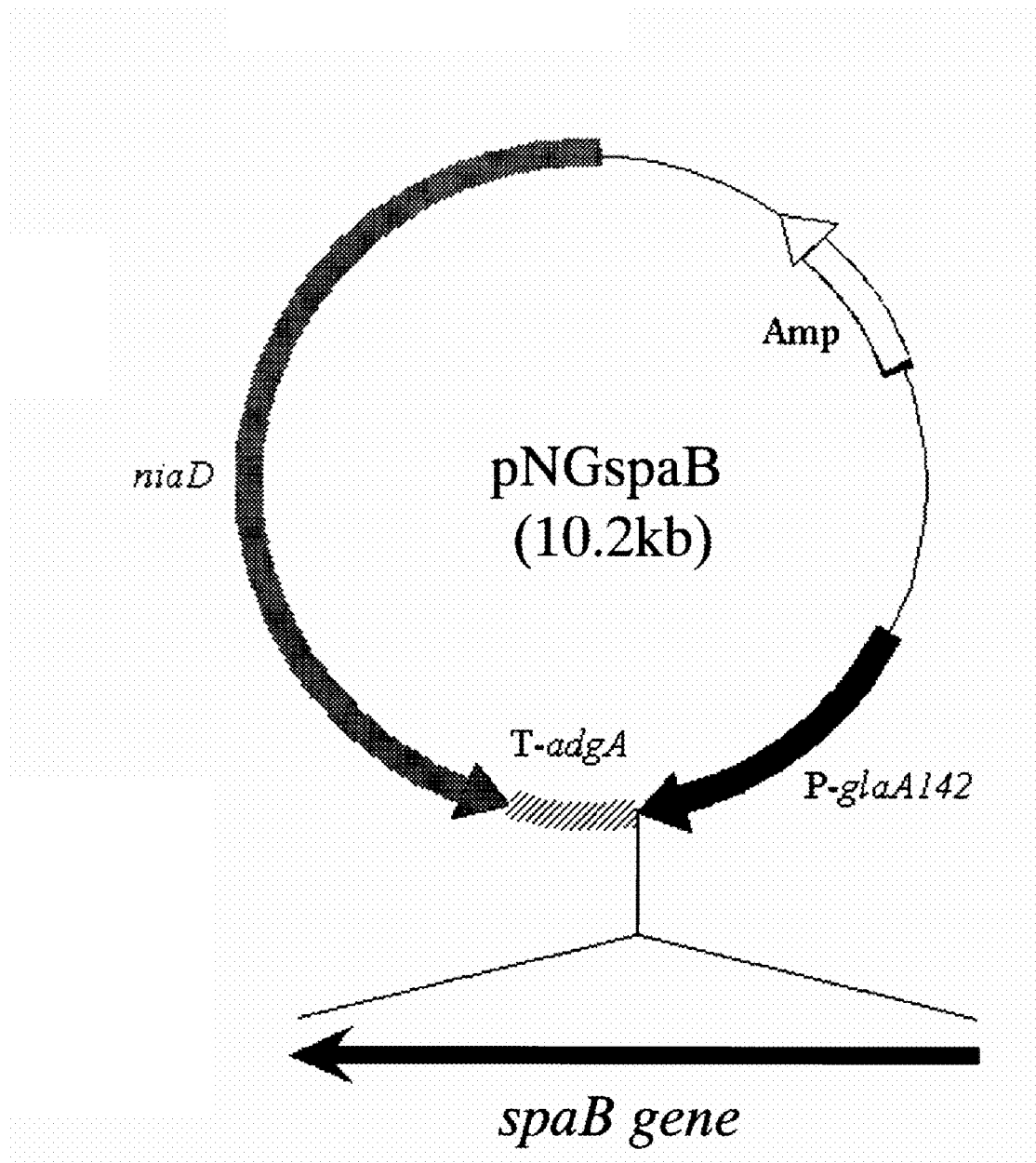
FIG. 2 is a schematic view showing a configuration of an expression vector pNGspaB.

Next, a plasmid pNGspaB for expressing phospholipase $A_2$-spaB in Aspergillus was constructed. Firstly, the phospholipase $A_2$-spaB gene cloned to pT-Blue obtained in Example 5 was digested with restriction enzymes Hind III and Xba I (Takara Shuzo Co. Ltd.) to obtain about 700 bp DNA fragment as an insert DNA. On the other hand, *Aspergillus* expression vector pNGA142 having niaD gene derived from *Aspergillus* as a selection marker, a modified promoter of a modified type glucoamylase gene derived from *Aspergillus* as a promoter and a terminator of α-glucosidase gene derived from *Aspergillus* as a terminator (Minetoki et al., Appl. Microbiol. Biotechnol., 50, 459-467 (1988)) was digested with Hind III and Xba I (Takara Shuzo Co. Ltd.). Thereafter, dephosphorylation was carried out with the use of Alkaline Phosphatase (Takara Shuzo Co. Ltd.) to obtain a vector DNA. The insert DNA and the vector DNA, which had been prepared as mentioned above, were ligated to each other with the use of Ligation Kit ver.2 (Takara Shuzo Co. Ltd.), thereby transforming *Escherichia coli* DH5α strain competent cell (TOYOBO) to obtain ampicillin resistant transformant. The plasmid carried by the obtained clone was called pNGspaB and used as an expression vector (see FIG. 2).

Example 9

Transformation of *Aspergillus*

A nitrate reductase deficient strain *Aspergillus oryzae* niaD300 strain (nitrate reductase deficient mutant of *Aspergillus oryzae* RIB-40 strain (ATCC 42149), Minetoki et al., Curr. Genet., 30, 432-438 (1996)) was cultured in a dextrin-peptone medium (2% dextrin, 1% polypeptone, 0.5% $KH_2PO_4$, 0.05% $MgSO_4$-$7H_2O$, pH 5.5) with shaking at 30° C. for 3 days. The obtained fungus bodies were washed with sterile water. The fungus bodies were suspended in a cell wall digestion solution [10 mM phosphate buffer solution, pH 6.0, 0.8M NaCl, 20 mg/ml Yatalase (Takara Shuzo Co. Ltd.)] and gently shaken at 30° C. for 2-3 hours so as to form a protoplast. The obtained protoplast was filtrated with a glass filter so as to remove the remaining fungus bodies.

Next, competent cells were prepared by using this protoplast by a method by Gomi et al. (Agric. Biol. Chem., 51, 323-328 (1987)), and transformed with the use of pNGA142 (control), pNGspaA or pNGspaB so as to obtain transformants that can be grown in a culture medium containing nitrate as a single nitrate source, for example, a Czapek-Dox medium (0.2% $NaNO_3$, 0.1% $KH_2PO_4$, 0.2% KCl, 0.05% $MgSO_4$-$7H_2O$, 0.002% $FeSO_4$-$7H_2O$, 2% glucose, pH 5.5). Four strains of transformants were obtained for each plasmid and 12 strains of transformants were obtained in total. The transformants derived from plasmids pNGA142, pNGspaA and pNGspaB were named vector 1 to vector 4, SpaA-1 to SpaA-4, and SpaB-1 to SpaB-4, respectively.

Example 10

Expression of Phospholipase $A_2$ by Phospholipase $A_2$-spaA Transformant

The obtained phospholipase $A_2$-spaA transformant was cultured in the below mentioned DPY culture medium with shaking at 30° C. for 3 days, and the culture solution was centrifuged at room temperature, 10,000×g, for 10 minutes so as to obtain a culture supernatant and fungus bodies. The fungus bodies were ground by the use of MultiBeads Shocker (Yasui Kikai). The resultant suspension was made to be a disrupted fungus suspension.

<DPY Medium>
  2% dextrin
  1% polypeptone
  0.5% yeast extract
  0.5% $KH_2PO_4$
  0.05% $MgSO_4$-$7H_2O$
  pH 5.5

Figure 3:
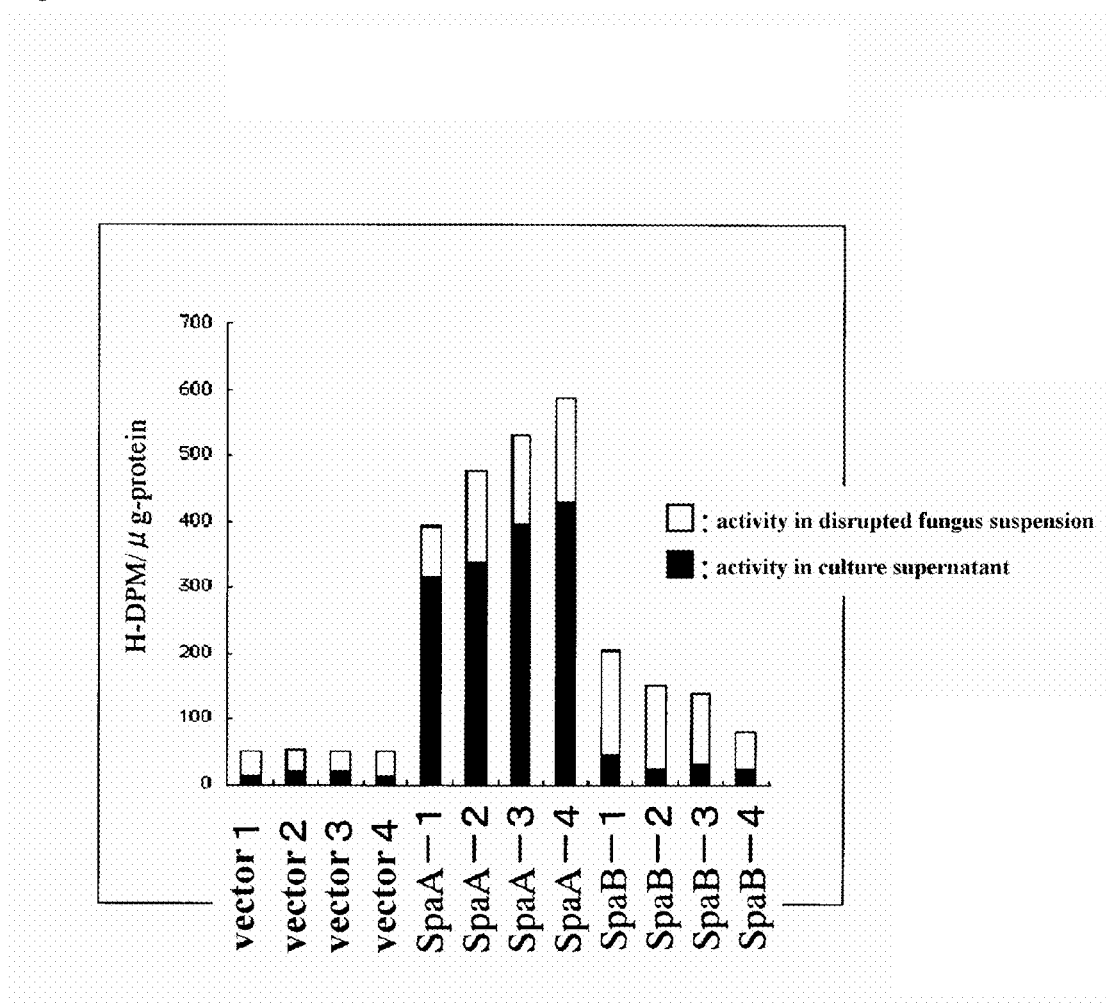
FIG. 3 is a graph showing the phospholipase activities (in culture supernatant and in disrupted fungus suspension) of phospholipase $A_2$-spaA transformant and phospholipase $A_2$-spaB transformant.

The phospholipase $A_2$ activities of the resultant culture supernatant and disrupted fungus suspension were measured by the following method. As a result, in particular, in the culture supernatant, remarkably higher phospholipase $A_2$ activity was confirmed as compared with control strains (i.e., vectors 1 to 4) (FIG. 3). As is apparent from this result, it was demonstrated that the obtained putative phospholipase $A_2$-spaA gene encoded phospholipase $A_2$.

(Enzyme Activity Measurement Method of Phospholipase $A_2$)

The measurement of phospholipase $A_2$ activity was carried out by a method for measuring the quantity of labeled oleic acid separated from the labeled *Escherichia coli* membrane in vivo (Elsbach, P., and Weiss, J. (1991) Methods Enzymol. 197, 24-31) added with some modification. That is to say, a reaction solution (final amount of liquid: 100 μl) consisting of *Escherichia coli* (~500,000 dpm) that had been labeled with $2.5 \times 10^8$ [$^3$H] oleic acid and then autoclaved, 25 mM Tris-HCl buffer (pH7.5) and 10 mM $CaCl_2$ and an enzyme solution was incubated at 30° C. for 30 minutes, 1% bovine serum albumin (w/v), which had been cooled on ice, was added and centrifugation (10,000×g) was carried out immediately after the addition. The radioactivity in the thus obtained supernatant was measured by the use of liquid scintillation counter. The enzyme activity (H-DPM/μg-protein) was calculated based on the counted number (H-DPM) measured under this condition. The *Escherichia coli* labeled with [$^3$H] oleic acid was prepared by the following method. 100 μl of culture solution of Eshcericia coli DH5α (strain that had been cultured in nutrient medium at 37° C. overnight was inoculated in a nutrient medium containing 10 ml of 5 μCi/ml of [$^3$H] oleic acid and incubated at 37° C. for 3 hours. The culture solution was centrifuged (at room temperature, 3,000×g, for 12 minutes) so as to collect fungus bodies. The collected fungus bodies were suspended in 10 ml of fresh medium and incubated at 37° C. for 30 minutes. The fungus bodies were collected by centrifugation (at room temperature, 3,000×g, for 12 minutes), washed with 5 ml of 1% bovine serum albumin (w/v), and finally suspended in an appropriate amount of distilled water at $5 \times 10^8$ cells/ml. Thus, *Escherichia coli* solution labeled with [$^3$H] oleic acid was obtained.

Example 11

Expression of Phospholipase A₂ by Phospholipase A₂-spaB Transformant

By carrying out culturing and treatment after culturing similar to Example 10 using Phospholipase A₂-spaB transformant, culture supernatant and disrupted fungus suspension of phospholipase A₂-spaB transformant were obtained. As compared with the case of phospholipase A₂-spaA transformant, the growth of transformant was remarkably inhibited. This was thought to be because a large amount of phospholipase A₂-spaB were expressed, resulting in inhibiting the fungus bodies.

Similar to the case of phospholipase A₂-spaA, the phospholipase A₂ activities of the obtained culture supernatant and disrupted fungus suspension were measured. As a result, in particular, in the disrupted fungus suspension, remarkably higher phospholipase A₂ activity was confirmed as compared with control strains (i.e., vectors 1 to 4) (FIG. 3). As is apparent from this result, it was demonstrated that the obtained putative phospholipase A₂-spaB gene encoded phospholipase A₂.

Example 12

Figure 4:
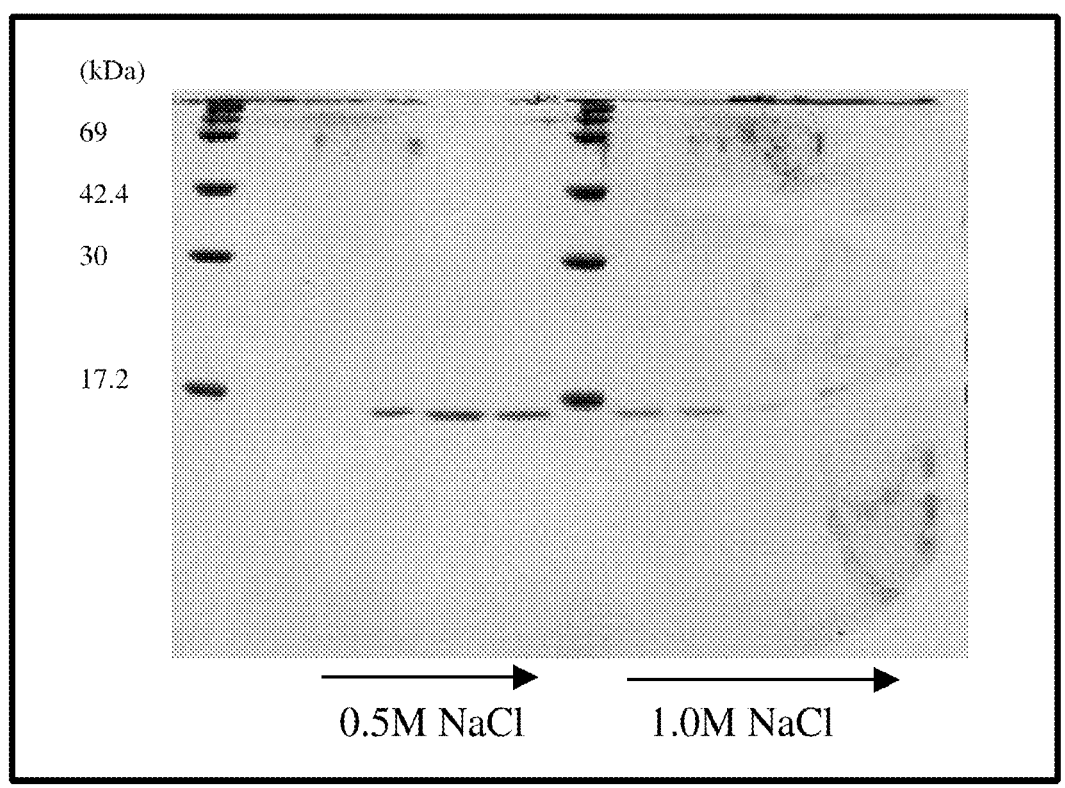
FIG. 4 is a view showing SDS-polyacrylamide gel electrophoresis patterns of phospholipase $A_2$-spaA protein purified from a transformant carrying a phospholipase $A_2$-spaA gene.
Figure 5:
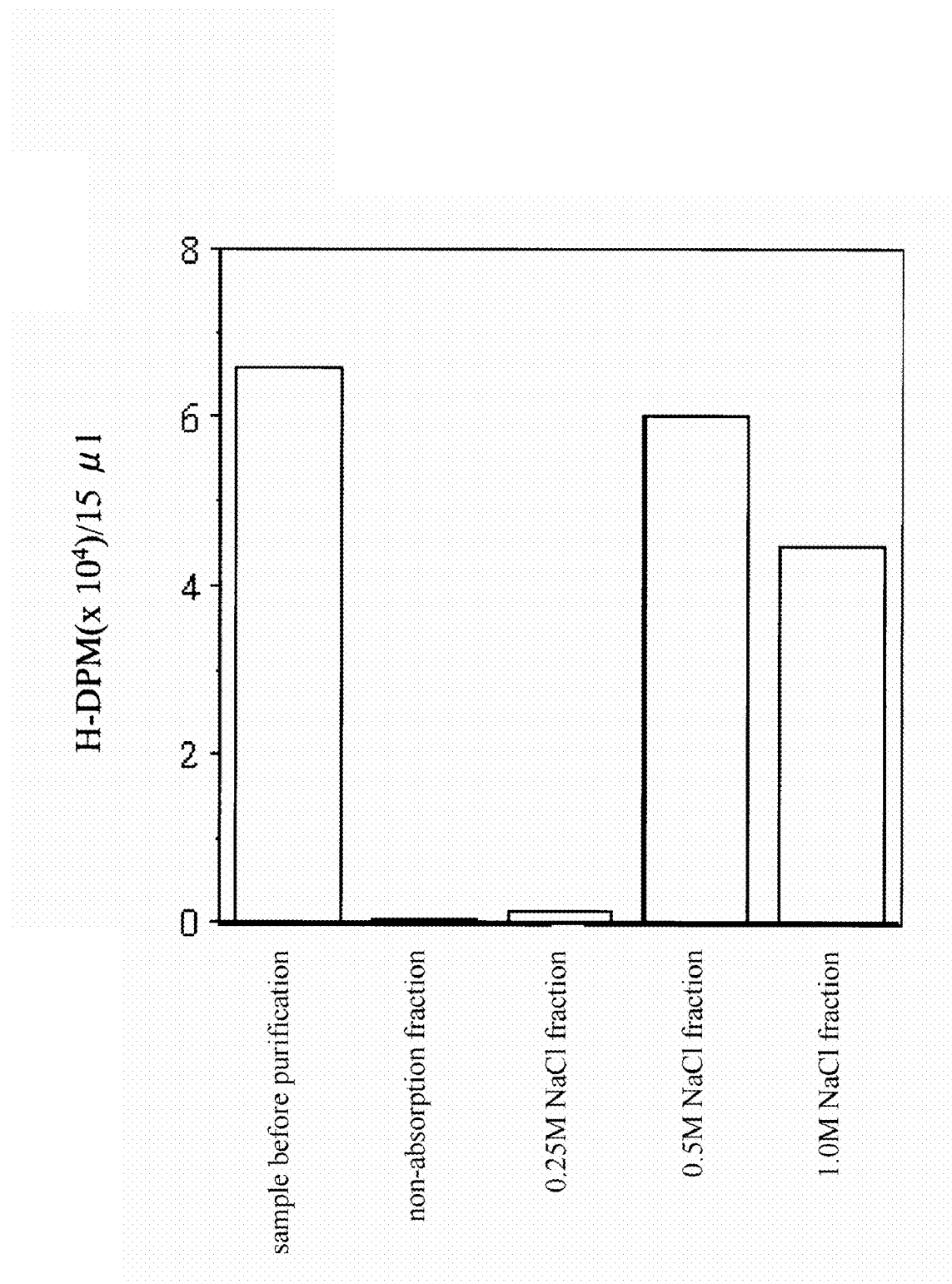
FIG. 5 is a graph showing the measurement results of phospholipase A2 activity using a culture supernatant of phospholipase $A_2$-spaA transformant purified by a CM-cellulose column.

Purification of Phospholipase A₂ Expressed by Phospholipase A₂-spaA Transformant 20 ml of culture supernatant of phospholipase A₂-spaA transformant obtained in Example 10 was diluted ten times with a 25 mM Tris-HCl buffer solution (pH 7.4), then subjected to CM-cellulose column chromatography that had been equilibrated with 25 mM Tris-HCl buffer solution (pH 7.4) and eluted with the use of the same buffer solution containing 0.1M, 0.25M, 0.5M and 1.0 DM NaCl by stepwise-gradient elution. Each eluate (10 µl) was subjected to SDS-polyacrylamide gel electrophoresis and stained with Coomassie brilliant blue. As a result, elution fraction at the NaCl concentration of 0.5-1.0 M, a single band of molar weight of about 16 kDa was detected (FIG. 4). The phospholipase A₂ activity of resultant non-adsorption fraction of 0.25M NaCl, 0.5M NaCl and 1.0M NaCl was measured. As a result, as shown in FIG. 5, the activity was found in 0.5M and 1.0M NaCl fraction. In the meanwhile, the activity hardly detected in non-adsorption and 0.25M NaCl fraction. Consequently, it was demonstrated that protein of molar weigh of 16 kDa eluted in the 0.5M and 1.0M NaCl fraction was phospholipase A₂.

The present invention is not particularly limited to the above-mentioned embodiments and descriptions of Examples of the present invention. Variations which are within the scope of the following claims and to which a person skilled in the art can achieve easily are also included in the present invention.

INDUSTRIAL APPLICABILITY

The present invention provides phospholipase A₂ derived from *Aspergillus* and DNA encoding the same. By using the DNA of the present invention, a production system of phospholipase A₂ using safer filamentous fungi was constructed.

---

The invention claimed is:

1. An isolated DNA selected from the group consisting of the following: (A) a DNA encoding phospholipase $A_2$ having the amino acid sequence of SEQ ID NO:2; and (B) a DNA encoding phospholipase $A_2$ having the amino acid sequence that is at least 95% identical to the full length amino acid sequence of SEQ ID NO:2.

2. A vector carrying the DNA according to claim 1.

3. Filamentous fungi into which the DNA according to claim 1 is exogenously introduced.

* * * * *